(12) United States Patent
Walker

(10) Patent No.: US 7,275,416 B2
(45) Date of Patent: Oct. 2, 2007

(54) VOLUMETRIC DENSIOMETER FLASK

(76) Inventor: Stephan Howard Walker, 4622 Farman St., North Charleston, SC (US) 29405

(*) Notice: Subject to any disclaimer, the term of this patent is extended or adjusted under 35 U.S.C. 154(b) by 208 days.

(21) Appl. No.: 11/063,359

(22) Filed: Feb. 23, 2005

(65) Prior Publication Data

US 2006/0185421 A1    Aug. 24, 2006

(51) Int. Cl.
  *G01N 9/00*  (2006.01)
  *G01F 19/00*  (2006.01)
(52) U.S. Cl. ....................... 73/32 R; 73/427
(58) Field of Classification Search ............... 73/32 R, 73/426, 427, 149, 61.41
  See application file for complete search history.

(56) References Cited

U.S. PATENT DOCUMENTS

| 150,113 | A |   | 4/1874 | Vom Hofe |
| 1,252,347 | A | * | 1/1918 | Homstead ............... 73/864.15 |
| 2,742,789 | A | * | 4/1956 | Seraphin ................. 73/427 |
| 3,880,012 | A | * | 4/1975 | Shapcott ................. 73/426 |
| 4,085,616 | A |   | 4/1978 | Patel et al. |
| 4,109,530 | A | * | 8/1978 | Kim ........................ 73/427 |
| 4,196,614 | A |   | 4/1980 | McLaughlin |
| 4,246,789 | A |   | 1/1981 | Olds |
| 4,262,535 | A |   | 4/1981 | Andersson |
| 4,287,760 | A | * | 9/1981 | Kubo et al. ............. 73/149 |
| 4,292,846 | A |   | 10/1981 | Barnett |
| 4,358,958 | A |   | 11/1982 | Wehrenberg |
| 4,928,514 | A | * | 5/1990 | Beaston ................. 73/1.73 |
| 5,445,023 | A |   | 8/1995 | Reed |
| 5,823,046 | A |   | 10/1998 | Schagerstrom et al. |
| 6,543,284 | B2 |   | 4/2003 | Hoeting et al. |
| 6,575,336 | B1 | * | 6/2003 | Bayer .................... 222/158 |
| 6,668,625 | B2 |   | 12/2003 | Weis et al. |
| 6,966,121 | B2 | * | 11/2005 | Bolle ..................... 33/494 |
| 2004/0226362 | A1 |   | 11/2004 | Marx et al. |

* cited by examiner

*Primary Examiner*—Helen Kwok
(74) *Attorney, Agent, or Firm*—Harleston Law Firm LLP

(57) ABSTRACT

A volumetric densiometer flask for determining the volumetric density of a solute includes:
  (a) a first bulbous portion in a lower end section of the flask;
  (b) a second bulbous portion in an upper end section of the flask, the second bulbous portion comprising an open mouth at its upper end;
  (c) a central neck comprising a central channel in open communication with the first bulbous portion at an upper end of the neck, and the second bulbous portion at an opposite, lower end of the neck; and
  (d) a removable stopper that is closely insertable into the mouth of the second bulbous portion, the mouth being correspondingly sized to a lower end of the stopper. Also included herein is a procedure for determining the volumetric density of a given sample using the volumetric densiometer flask.

19 Claims, 5 Drawing Sheets

US 7,275,416 B2

VOLUMETRIC DENSIOMETER FLASK

CROSS REFERENCE TO RELATED DOCUMENT

This invention was described in Disclosure Document Number 539823, which was received by the U.S. Patent & Trademark Office on Oct. 9, 2003.

BACKGROUND OF THE INVENTION

1. Technical Field

The present invention relates to a volumetric densiometer laboratory flask for determining the volumetric density of a chemical in solution.

1. Background Information

Conventional laboratory methods are available for determining the volumetric density of a particular chemical in solution for use in concentration calculations. However, such methods are not as accurate as they could be, and sometimes result in inaccurate density determinations.

It has been found herein that since solutions expand or contract depending on the characteristics of the particular solution, a volumetric densiometer flask that allows such reactions to take place and facilitates measurements after the reaction would be quite useful. The volumetric densiometer flask of the present invention allows for a more accurate determination of volumetric density of a solute or chemical.

BRIEF SUMMARY OF THE INVENTION

The present invention is a volumetric laboratory flask for determining the density of a chemical that has been solubilized in solution. The present volumetric densiometer flask includes:

(a) a first bulbous portion in a lower end section of the flask;

(b) a second bulbous portion in an upper end section of the flask, the second bulbous portion comprising an open mouth at its upper end;

(c) a central neck comprising a central channel in open communication at an upper end of the neck with the second bulbous portion, and the first bulbous portion at an opposite, lower end of the neck; and (d) a removable stopper that is closely insertable into the mouth of the second bulbous portion, the mouth being correspondingly sized to a lower end section of the stopper. The flask has a number of graduated markings on the neck. The narrow channel in the neck preferably has an inside diameter of between about 0.25 centimeters and about 0.50 centimeters.

Advantages of the present invention also include the following:

1) allows for a more accurate determination of volumetric density of a solute or chemical, when compared to conventional methods for determining volumetric density;

2) allows for rapid scale-up in a plant;

3) fast, safe, and reliable; and 4) improved resolution and more precise, predictable laboratory results.

Also included herein is a procedure for determining volumetric density, the procedure comprising the steps of:

(a) Measuring out the sample;

(b) Pouring a solvent in through an open mouth of a volumetric densiometer flask, shaking it down to a first bulbous portion of the flask and bringing a meniscus of the solvent to a pre-determined zero mark on a neck of the flask;

(c) Closing the mouth of the flask, inverting the flask so the solvent flows to a second bulbous portion of the flask, returning the flask to an upright position, opening the flask mouth, and adding the sample through the open flask mouth;

(d) Closing and shaking the flask to substantially dissolve or solubilize the sample; and (e) Shaking the resulting solution down through a neck channel of the flask into the first bulbous portion, and taking a reading using graduated markings on the neck. Preferably, the procedure is repeated three times, and a statistical analysis is performed on the results.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein.

DETAILED DESCRIPTION OF THE INVENTION

Figure 1:
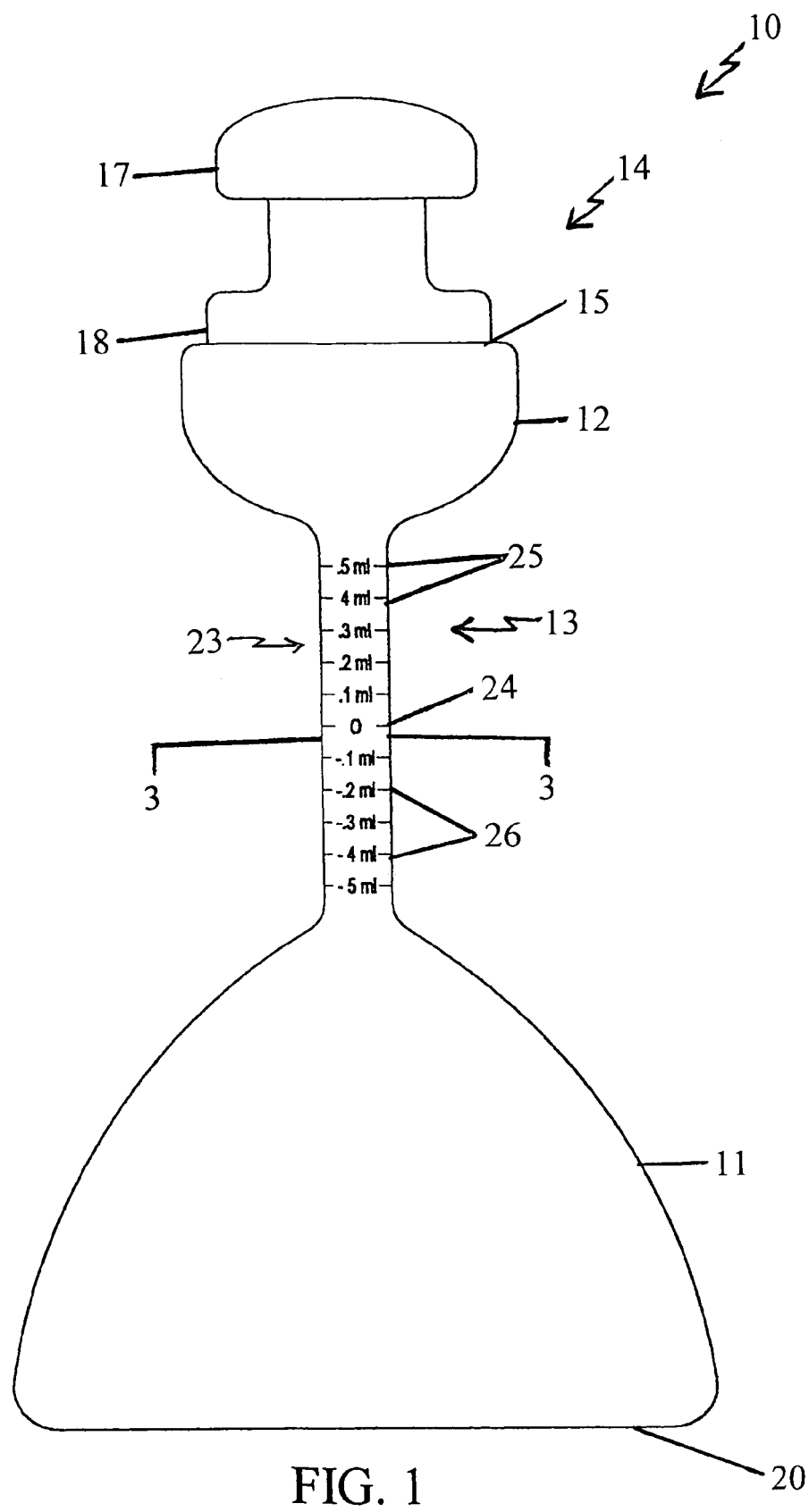
FIG. 1 is a front elevation view of a volumetric densiometer laboratory flask according to the present invention.

In the following description, like reference characters designate like or corresponding parts throughout the several views. Also, in the following description, it is to be understood that such terms as "back," "within," and the like are words of convenience and are not to be construed as limiting terms. Referring in more detail to the drawings, the invention will now be described.

Figure 2:
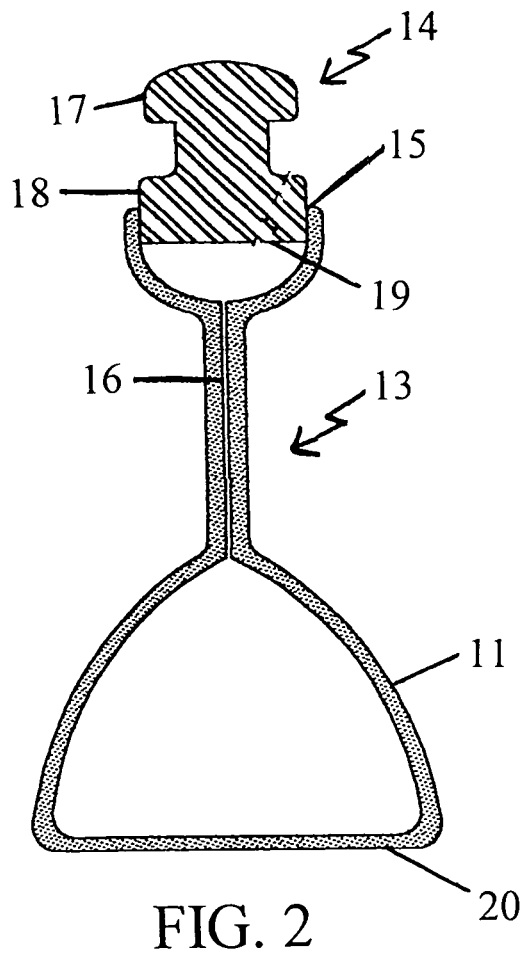
FIG. 2 is a longitudinal cross-section view of the volumetric densiometer laboratory flask according to FIG. 1.

Referring to FIGS. 1 and 2, a volumetric densiometer laboratory vessel, or flask, according to the present invention, which is generally referred to herein as 10, comprises:

(a) a first bulbous portion 11 in a lower end section of the flask 10;

(b) a second bulbous portion 12 in an upper end section of the flask 10;

(c) a central neck 13 with a narrow central channel 16 in open communication at an upper end of the neck 13 with the first bulbous portion 11, and the second bulbous portion 12 at an opposite, lower end of the neck 13; and (d) a removable stopper 14. The second bulbous portion 12 has an open, circular-shaped mouth 15 at its upper end. The mouth 15 is correspondingly sized to fit a lower end section 18 of the stopper 14. The stopper 14 is closely insertable into the mouth 15 of the second bulbous portion 11.

The first bulbous portion 11 is substantially larger than the second bulbous portion 12, as seen in FIGS. 1 and 2, in order to provide space for a fixed volume (50 ml., 100 ml., or 150 ml., for example) in the lower portion, and allow adequate space in the first bulbous portion (e.g., 25 ml., 50 ml., 75 ml., respectively) for shaking once the solvent and chemical have been added to the flask. The second bulbous portion 12 is in open communication with the first bulbous portion 11 via the narrow channel 16 in the neck 13. The diameter of the second bulbous portion 12 at its widest point is preferably about one-third to one-half the diameter of the first bulbous portion 11 at its widest point. The height of the flask may vary. A lower end of the neck 13 connects to the upper end of the first bulbous portion 11, while the opposite, upper end of the neck 13 connects to the lower end of the second bulbous portion 12.

The first bulbous portion 11 preferably holds a fixed volume between about 50 milliliters (ml.) and about 250 ml. The second bulbous portion 12 preferably holds at least ¼ as much liquid volume as the first bulbous portion 11. The flasks are more preferably 50 ml., 100 ml., 150 ml., or 250 ml. flasks. Most preferably, the first bulbous portion 11 holds twice as much liquid volume as the second bulbous portion 12. Thus, if the first bulbous portion holds 50 ml. (up to the zero mark, see below), the second bulbous portion most preferably holds about 25 ml. If the first bulbous portion holds 100 ml. (up to the zero mark, see below), the second bulbous portion most preferably holds about 50 ml., and so forth. The capacity of the second bulbous portion need not be as precise as the size of the first bulbous portion, since it is not filled to capacity. If both portions of the flask were filled to capacity, it would be difficult to shake it. It has been found herein that the maximum capacity of the first bulbous portion is preferably about 250 ml., and the minimum capacity of the first bulbous portion is preferably 25 ml.

When the volumetric densiometer flask 10 is in use, the solute or chemical to be tested, and the chosen solvent into which it will be dissolved, are each poured into the flask 10 via the open mouth 15 of the flask. The stopper 14 is then placed in the flask 10 and the flask is shaken, preferably by hand.

Figure 3:
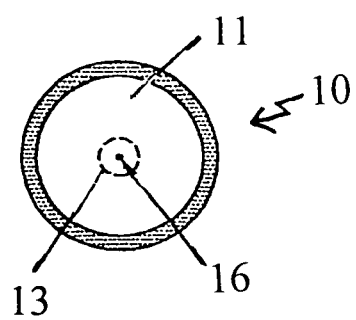
FIG. 3 is a latitudinal cross-section view of a neck of the densiometer flask according to FIG. 1.

As illustrated in FIGS. 2 and 3, the narrow central channel 16 extends through the neck 13. The neck 13 and channel 16 are preferably straight, each with an even diameter all the way through their length, as depicted in FIG. 2. Importantly, the length of the neck 13, and therefore the channel, is dependent upon the diameter of the neck channel 16 (see FIG. 2). Generally, the smaller the channel diameter is, the longer the neck length is. The length of the neck 13 is preferably about equal to the height of the first bulbous portion 11.

In the volumetric laboratory flask 10 depicted in FIGS. 1 and 2, the first bulbous portion 11 is generally hemispherical in shape (shaped like an inverted wine glass), with a substantially planar base 20 so that the flask 10 can be rested on a planar surface such as a laboratory table top. The bottom of the flask may alternatively be rounded, where the volumetric laboratory flask will be held or clamped to a stand. The second bulbous portion 12 is preferably generally semi-spherical in shape, as shown in FIGS. 1 and 2. This is advantageous in that it facilitates mixing of the solute or chemical to be tested into the chosen solvent, and then facilitates passage of the solution down the neck to the first bulbous portion, without any sticking of small unsolubilized particles of the chemical to the sides of the vessel. A semi-spherical shape is preferred for the second bulbous portion 12, so that the flask mouth 15 is wide enough to easily accommodate the selected solvent and the solute or chemical to be tested. The smooth inside sides of the second bulbous portion guide the solution down to the neck channel 16.

As seen in FIGS. 1 and 2, the flask stopper 14 comprises an upper handle section 17 that permits a user to grip the stopper 14 and insert it or remove it from the flask 10. The stopper 14 also includes a cylindrically shaped lower section 18, which preferably has smooth sides that fit closely into the correspondingly sized mouth 15. The removable stopper 14 is sized to fit closely into the flask mouth 15 so that the flask can be shaken without losing any of the solution. The stopper 14 preferably has a planar bottom 19, which does not extend down into the second bulbous portion. If the stopper was to extend down into the solution in the flask, it could adversely affect the reading when the flask is in use.

In use, the stopper 14 is removed from the volumetric laboratory flask 10 and the desired solvent is poured in through the open mouth 15 of the flask. A pre-determined amount of the solute, or other chemical to be tested, is added through the mouth 15 into the second, bulbous portion 12. If desired, the chemical may be pre-mixed in a small, fixed amount of the solvent prior to its addition to the flask. The stopper 14 is then placed in the mouth 15 of the volumetric flask 10, and the flask is shaken, preferably up and down, which mixes the solution, speeds the reaction, and forces the solution down through the narrow neck channel 16 into the first bulbous portion 11.

Figure 4:
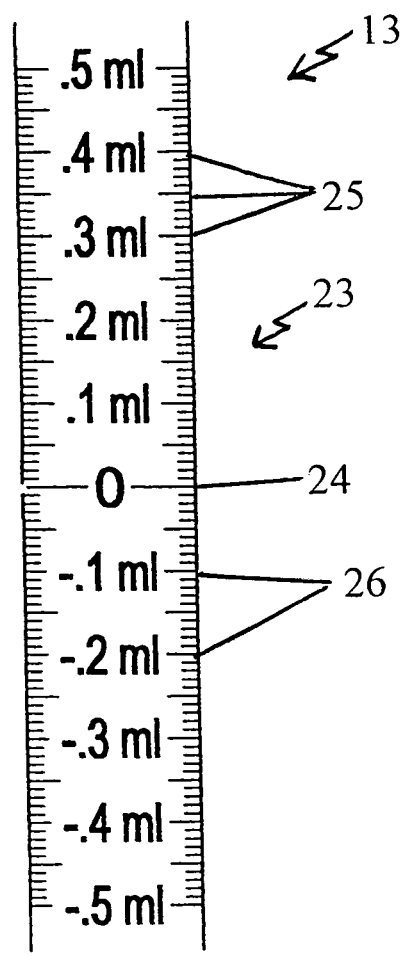
FIG. 4 is a front elevation view of a portion of a neck of the densiometer flask according to FIG. 1.

Referring to FIGS. 1 and 4, the outside of the neck 13 of the laboratory flask 10 has a number of graduated markings 23 for measurement purposes. The markings include a zero mark 24, first volumes 25 exceeding the zero mark in tenths of a milliliter, and second volumes 26 less than the zero mark in tenths of a milliliter. When the flask 10 is filled with a liquid to the zero mark 24, the volume of the liquid contained within the flask 10 is equal to the capacity of the first bulbous portion 11 and a portion of the neck 13 (i.e., 50 milliliters in the flasks shown in FIGS. 1 and 2). The graduated markings 23 may alternatively demarcate hundredths of a milliliter, or other suitable measurements. The flask neck 13 is preferably between about two and about four inches in length. In general, the longer the flask neck is, the narrower the neck channel is.

The following formula is used to derive the diameter of the flask neck. An example where the length of the neck has been determined follows the formula.

$$\Pi r^2 h = v$$

$$\Pi r^2 (5.08 \text{ cm}) = 1 \text{ cm}^3$$

$$\Pi r^2 = 0.197 \text{ cm}^2$$

$$r^2 = \frac{0.197 \text{ cm}^2}{3.14}$$

$$\sqrt{r^2} = \sqrt{0.0627 \text{ cm}^2}$$

$$r = 0.250 \text{ cm}$$

$$r = 2.50 \text{ mm}$$

$$D = 5.00 \text{ mm}$$

Where: r=radius of the central channel; h=height of the neck, such as 2 inches; v=volume of the neck; D=diameter; cm=centimeters; and mm=millimeters.

If appropriate, the volumetric laboratory flask 10 may be calibrated prior to the addition of the chemicals into the flask 10, for example, by pouring 50 milliliters of water into the flask 10 and shaking it down to the first bulbous portion 11. The meniscus of the water should be at the zero mark 24.

The volumetric laboratory flask 10 can be utilized to calculate the volumetric density of a solute that ionizes in solution. In use, an exact volume of solvent is added to the flask 10, such that the meniscus of the solvent is located at the zero marking. A known mass of solute, such as potassium chloride (KCl) or sodium hydroxide (NaOH), or another chemical (e.g., a granular or powdered chemical) is then added to the solvent, the stopper 14 is placed in the flask 10, and the flask 10 is shaken. The chemical may be a solid (e.g., powdered, granular), or a liquid, for example, an acid, base, or salt. The selected solvent is any suitable analyte the solute is soluble in, such as deionized water, or an acid mixture (most preferably a 7:3 mixture of nitric acid and hydrochloric acid, such as Aqua Regia).

Ionization of the solute in the solvent causes an exothermic or endothermic reaction. An exothermic or endothermic response indicates that the order of the water molecules in solution is changing, and that electrostatic attractions exist between the ions and molecules of solute and solvent. Thus, the density of the solute in solution is different from the density of the solute out of solution. The solution is allowed to equilibrate at standard temperature and pressure (STP) and the user then reads the volume, preferably in tenths or hundredths of a milliliter, from the graduated markings 23. This volume is the volume of the solute in solution. Both the weight and volume of the solute are extrapolated mathematically to one milliliter.

It has been found herein that a neck channel 16 with an inside diameter of between about 0.25 centimeters and about 0.50 centimeters works best in the flask 10. This diameter has been found to be large enough to allow the chemical in its solvent to trickle down the neck channel 16, yet narrow enough: 1) to retain the chemical and solvent in the second bulbous portion for a sufficient amount of time to mix or solubilize; and 2) once the solution has been shaken down to the first bulbous portion 11, for an observer to examine the meniscus in the neck channel and derive a precise measurement.

The volumetric laboratory flask 10 is preferably made of glass or another transparent material, so that the meniscus and the solution in the flask can easily be seen. The flask neck 13 is most preferably between about 0.5 and about four inches long, more preferably between about two and three inches. Since the flask is intended to be shaken, the glass walls of the neck are preferably relatively thick, so the neck is not likely to snap during shaking. The neck is preferably made of glass so the meniscus of the liquid in the channel can easily be viewed through the neck. The glass neck preferably has an outside diameter of between about two and five centimeters.

Normally, the solution is prepared in a beaker using pipettes to bring the solution up to volume. Use of this volumetric densiometer flask 10 eliminates the necessity of utilizing a separate, conventional volumetric flask. Here, two steps can be accomplished in one flask. In comparison to conventional testing methods, use of this volumetric densiometer flask 10 saves time cleaning glassware and conducting volumetric density tests. When the present flask is used, the tests are also more accurate in comparison to currently used conventional testing methods. Also, the flask is safe regardless of whether the reaction inside it is endothermic or exothermic.

The following equation is then solved for the volumetric density of the solute:

$$A/[B(C) \pm D(E)] = F$$

where:
A=mass of the solute in µg (micrograms);
B=volume of the solvent in milliliters (ml);
C=density of the solvent in g/ml (grams/milliliter);
D=volume of the solute in milliliters (ml);
E=volumetric density of the solute in g/ml; and
F=concentration of the solution in µg/g.

A preferred procedure herein for determining the volumetric density of a given sample includes the following steps:

(a) Measuring out (e.g., weighing) the sample to be determined;

(b) Pouring a solvent in through an open mouth 15 of a volumetric densiometer flask 10, shaking it down to a first bulbous portion 11 of the flask 10, and bringing a meniscus of the solvent to a pre-determined zero mark 24 on a neck 13 of the flask 10 (preferably by using a dropper to drop solvent into the flask until the meniscus lies on the zero mark);

(c) Closing the mouth 15 of the flask 10 (e.g., by inserting the stopper in the mouth), turning the flask 10 upside down so the solvent flows to a second bulbous portion 12 of the flask 10, and back again, opening the flask mouth (preferably by removing the stopper 14), and adding the sample through the open flask mouth 15;

(d) Closing and shaking the flask 10 to substantially dissolve or solubilize the sample in the solvent; and (e) Shaking the resulting solution down through a neck channel 16 of the flask 10 into the first bulbous portion 11, and preferably taking a reading using graduated markings 23 on the neck 13. The procedure preferably also includes the step of:

(f) Performing three trials, and performing a statistical analysis on the results from the three trials to reject or retain the results from each trial. Once the flask has been cleaned, this procedure can be repeated for the next sample. Once the measurement is derived for a particular sample/solute, it is not necessary to repeat the test. The solvent is preferably deionized water, or a mixture of acids such as nitric acid and hydrochloric acid.

When an exothermic reaction takes place in the flask, the technician subtracts the volume of the solute times milliliters times grams per milliliter [(ml.) (g./ml.)], which equals the number of grams in solution. When it is instead an endothermic reaction, the technician adds the volume of the solute times milliliters times grams per milliliter [(ml.) (g./ml.)], which equals the number of grams in solution.

The first bulbous portion 11 most preferably holds 50 milliliters of liquid (with the meniscus of the liquid at the zero marking 24). The second bulbous portion 12 most preferably holds about 20 or 30 milliliters of liquid. Pouring this amount of solvent in the second bulbous portion 12 allows rapid dissolution of the solute in the solvent. The entire flask 10 preferably holds between about 50 and about 150 milliliters of liquid.

Figure 5:
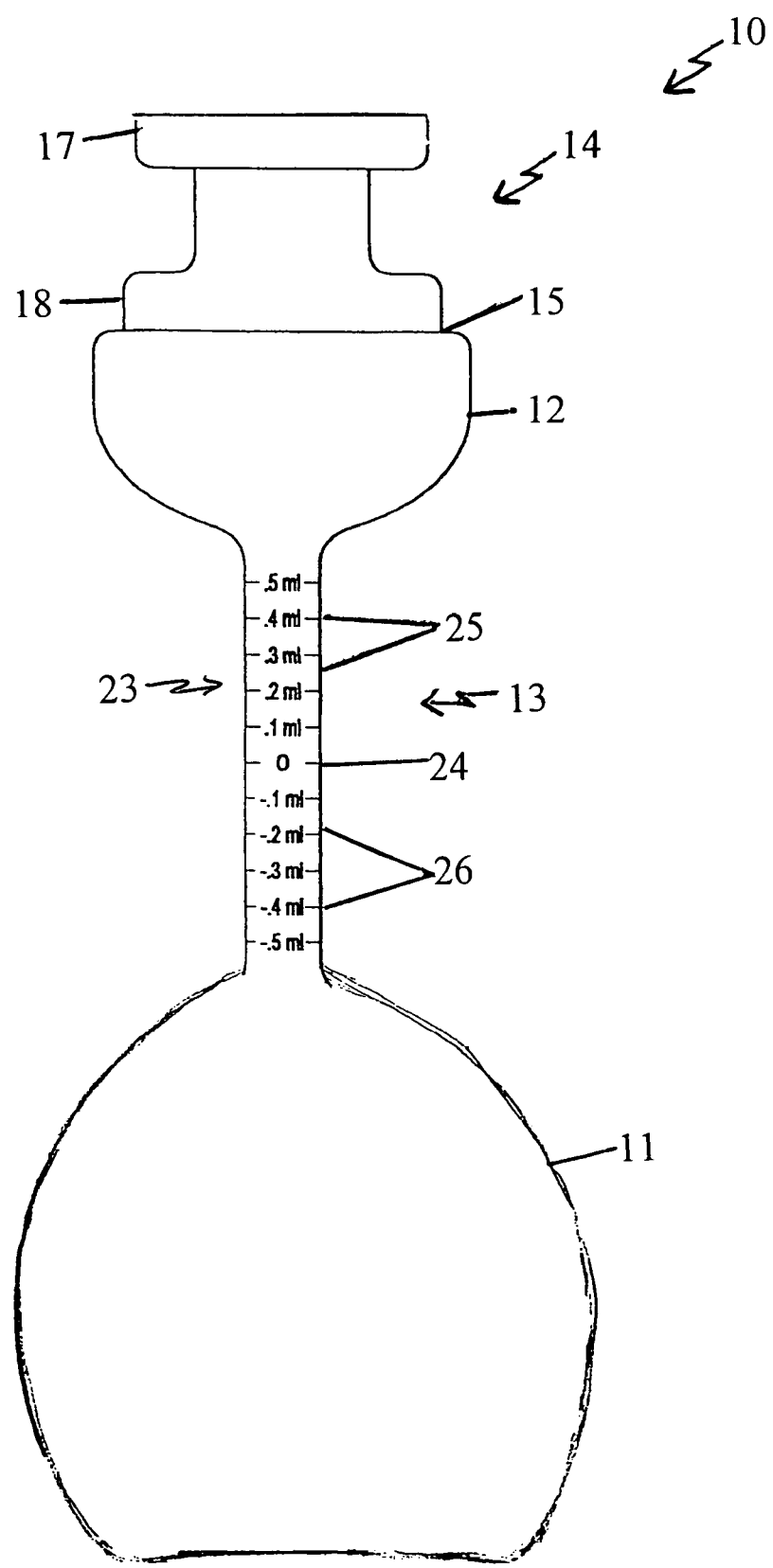
FIG. 5 is a front elevation view of a volumetric densiometer laboratory flask according to the present invention, shown with a stopper.

Referring to FIG. 5, the first bulbous portion 11 may be shaped like an inverted water goblet. The handle section 17 of the stopper 14 may have any shape that is suitable for grasping. The stopper 14 may be made of glass or rubber, or any other suitable material that will not be broken down over time by the various solvents and solutes used in the flask.

Figure 6:
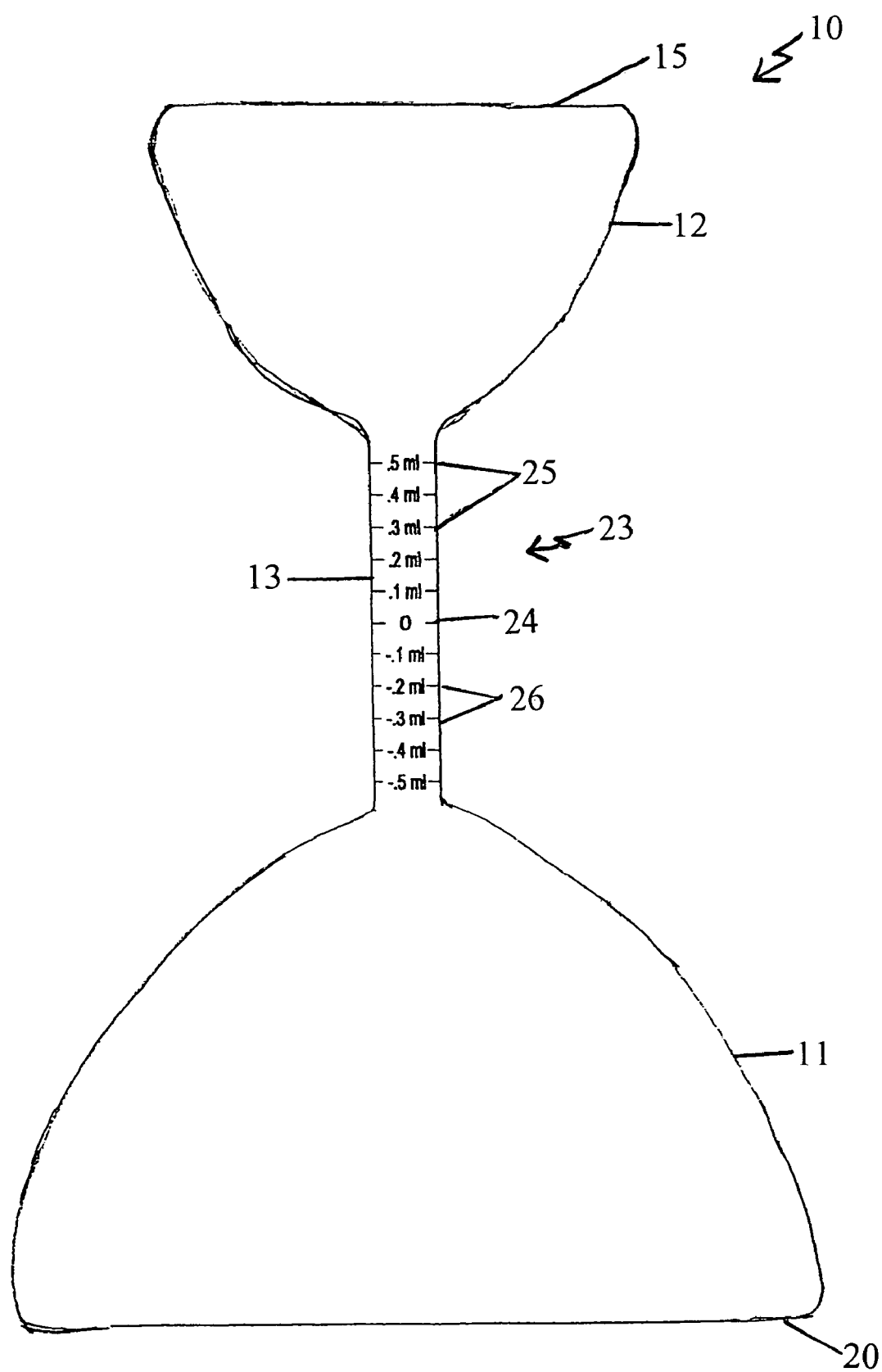
FIG. 6 is a front elevation view of a volumetric densiometer laboratory flask according to the present invention, shown without a stopper.
Figure 7:
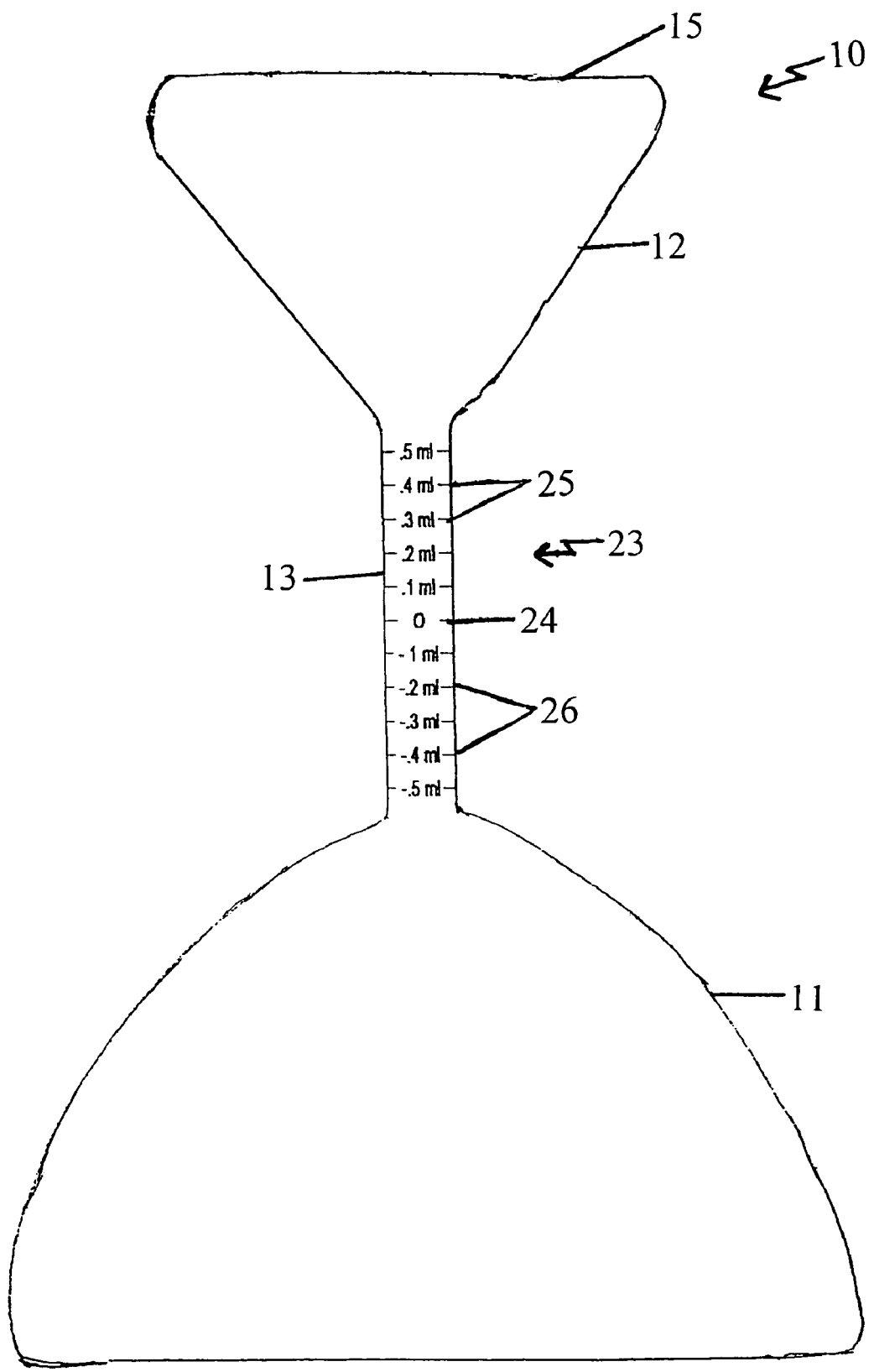
FIG. 7 is a front elevation view of a volumetric densiometer laboratory flask according to the present invention, shown without a stopper.

Referring to FIGS. 6 and 7, the second bulbous portion 12 may be shaped like a wine glass. The first bulbous portion 11 has a wide base 20 for stability when the base 20 of the flask 10 is resting on a table or other planar surface. Having a base that is wider than the rest of (any other part of) the flask is particularly useful when the solution is still in motion just after the flask has been shaken. The diameter of the flask mouth 15 is preferably between about one-third and about one-half the diameter of the flask base 20.

As shown in FIG. 7, the second bulbous portion 12 may be funnel-shaped to encourage the solution to flow toward the channel in the neck. This volumetric densiometer flask 10 shape is also advantageous in that the mouth is wide, which facilitates pouring the chosen solvent and the solute or other type of chemical to be tested into the second bulbous portion.

The volumetric densiometer flask of the present invention has a variety of applications, particularly where very low levels of a chemical or the like (e.g., parts per billion) are common and difficult to quantitate. The flask of the present invention is useful for testing groundwater and ensuring that the groundwater is in compliance with national pollutant discharge elimination limitations. For example, the present flask can be used for testing levels of heavy metals, such as mercury or zinc, in discharge waters. This lowers minimum detectable concentrations (MDCs).

The volumetric densiometer flask 10 can be used in chemical plant labs, and pharmaceutical plant labs, for example. The volumetric laboratory flask 10 is useful in environmental laboratories, allowing minimum detectable concentrations to be decreased and yet still be measurable using existing instrumentation. Minimum detectable activities for radioactive compounds can also be decreased and yet be measurable using the flask of the present invention. The flask of the present invention can also be used for increased sensitivity of electrical components in instrumentation. Preferably, the flask 10 itself does not include any other structural elements besides the two bulbous portions 11, 12 and the neck 13.

The following examples are intended to further illustrate the invention and facilitate its understanding. These examples are given solely for the purposes of illustration and are not to be construed as limiting the present invention in any way.

EXAMPLE I

Exemplifying the procedure described hereinabove, 100 ml. of deionized water is poured into the mouth of a volumetric densiometer flask according to the present invention at standard temperature and pressure. The solvent (water) is shaken down to the first bulbous portion, and the meniscus of the solvent is brought up to the zero marking on the neck of the flask using a small amount of the solvent in a dropper. The stopper is then inserted in the mouth and the flask is inverted to return the solvent to the second bulbous portion. (The second bulbous portion accommodates 25 milliliters of solvent.) The flask is placed on a table, the stopper is removed, and a 0.002 gram sample of reagent grade potassium chloride is poured into the mouth of the same flask. The stopper is inserted and the flask is shaken by hand. The flask with this solution is placed in a standard temperature (78 degrees Fahrenheit or 20 degrees Celsius) water bath and allowed to settle for about fifteen minutes.

A reading is taken at eye level using the graduated markings on the flask neck. The meniscus of the solution in the flask is observed at the 0.02 ml. level mark.

The following formula is used to derive a result. The volume of the solute in ml. (B) is obtained by inverting the density of the solvent in g/ml. (C) and multiplying by the weight of the solute added. The density of potassium chloride is 2.73 grams per cubic centimeter.

$$A/[B(C) \pm D(E)] = F$$

where:

A=mass of the solute in μg (micrograms);
B=volume of the solvent in milliliters (ml);
C=density of the solvent in g/ml (grams/milliliter);
D=volume of the solute in milliliters (ml);
E=volumetric density of the solute in g/ml; and
F=concentration of the solution in μg/g (micrograms/gram).

Since an endothermic reaction is taking place in the flask, the technician adds the volume of the solute times milliliters times grams per milliliter [(ml.) (g/ml.)], which equals the number of grams in solution.

This test is repeated three times and a statistical analysis is performed to reject or retain results.

EXAMPLE II

A 50 ml. mixture of concentrated 70% nitric acid and 30% hydrochloric acid (Aqua Regia) is poured into the mouth of a volumetric densiometer flask according to the present invention at standard temperature and pressure. The solvent (the acids) is shaken down to the first bulbous portion, and the meniscus of the solvent is brought up to the zero marking on the neck of the flask using a small amount of the solvent in a dropper. The stopper is inserted in the mouth of the flask, and the flask is inverted to return the solvent to the second bulbous portion. The second bulbous portion of this flask accommodates 25 milliliters of liquid. The bottom of the flask is then placed on a table, the stopper is removed, and a 1.0 milligram sample of elemental iron is poured into the mouth of the same flask. The stopper is again inserted and the flask is shaken by hand. The flask with this solution is placed in a standard temperature (78 degrees Fahrenheit or 20 degrees Celsius) water bath, and allowed to equilibrate for about ten minutes. A reading is taken at eye level using the graduated markings on the flask neck.

The formula provided in Example I is used to derive a result. The volume of the solute in ml. (B) is obtained by inverting the density of the solvent in g/ml. (C) and multiplying by the weight of the solute added. The flask is warm to the touch when the flask is shaken, indicating an exothermic reaction. Since an exothermic reaction is taking place in the flask, the technician subtracts the (volume of the solute) times (milliliters) times (grams per milliliter), which equals the number of grams in solution. The test is repeated three times and a statistical analysis is performed to reject or retain results.

From the foregoing it can be realized that the described flask of the present invention may be easily and conveniently utilized as a volumetric laboratory flask for measuring density of a solute. It is to be understood that any dimensions given herein are illustrative, and are not meant to be limiting. All ratios, parts, percentages, proportions, and other amounts stated herein are on a weight basis, unless otherwise stated herein, or otherwise obvious to one skilled in the art to which the invention pertains. All temperatures herein are in degrees Fahrenheit, unless otherwise stated herein.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

BRIEF LIST OF REFERENCE NUMBERS USED IN THE DRAWINGS 10 volumetric densiometer flask
11 first bulbous portion
12 second bulbous portion
13 neck
14 stopper
15 mouth
16 neck channel
17 stopper handle section
18 stopper lower section
19 bottom of stopper
20 base of flask
23 graduated markings
24 zero mark
25 first volumes
26 second volumes

What is claimed is:

1. A volumetric densiometer flask for determining a volumetric density of a solute, the flask comprising:
   (a) a first bulbous portion in a lower end section of the flask;
   (b) a second bulbous portion in an upper end section of the flask, the second bulbous portion comprising an open mouth at an upper end of the bulbous portion;
   (c) a central neck comprising a central channel in open communication with the second bulbous portion at an upper end of the neck, and the first bulbous portion at an opposite, lower end of the neck; and
   (d) a single, removable stopper that is closely insertable into the mouth of the second bulbous portion, the mouth being correspondingly sized to a lower end of the stopper; and wherein the flask comprises a plurality of graduated markings on the neck; and wherein the following is solved to obtain the volumetric density of the solute;

$$A/[B(C)\pm D(E)]=F$$

where: A=mass of the solute in micrograms; B=volume of a solvent in milliliters; C=density of the solvent in grams/milliliter; D=volume of the solute in milliliters; E=volumetric density of the solute in grains/milliliter; and F=concentration of the solution in micrograms/gram; and wherein, when the flask is in use, the solute and solvent are introduced through the oven mouth into the first bulbous portion and flow through the neck into the second bulbous portion.

2. The volumetric densiometer flask according to claim 1, wherein the channel in the neck has an inside diameter of between about 0.25 centimeters and about 0.50 centimeters.

3. The volumetric densiometer flask according to claim 1, wherein the first bulbous portion is at least twice as large as the second bulbous portion.

4. The volumetric densiometer flask according to claim 2, wherein the neck and the neck channel are substantially straight, each having an even diameter.

5. The volumetric densiometer flask according to claim 1, wherein a length of the neck is about equal to a height of the first bulbous portion.

6. The volumetric densiometer flask according to claim 1, wherein the second bulbous portion is funnel-shaped.

7. The volumetric densiometer flask according to claim 1, wherein a diameter of the second bulbous portion at a widest point of the second bulbous portion is between about one-third and about one-half the diameter of the first bulbous portion at a widest point of the first bulbous portion.

8. The volumetric densiometer flask according to claim 4, wherein the neck is between about 0.5 and about four inches in length.

9. The volumetric densiometer flask according to claim 1, wherein the removable stopper comprises an upper handle section, and a cylindrical-shaped lower section, which is closely insertable into the correspondingly sized mouth.

10. The volumetric densiometer flask according to claim 1, wherein the stopper comprises a planar bottom, which does not extend down into the second bulbous portion of the flask.

11. The volumetric densiometer flask according to claim 1, wherein the first bulbous portion holds a fixed volume of between about 50 milliliters and about 250 milliliters, and the second bulbous portion holds at least ¼ as much liquid volume as the first bulbous portion.

12. The volumetric densiometer flask according to claim 1, wherein a base of the flask is wider than the rest of the flask, and the second bulbous portion is generally hemispherical in shape.

13. A process for determining a volumetric density of a given sample, the process comprising the steps of:
   (a) Pouring a solvent in through an open mouth of a volumetric densiometer flask, shaking the solvent down to a first bulbous portion of the flask, and bringing a meniscus of the solvent to a pre-determined zero mark on a neck of the flask;
   (b) Closing the mouth of the flask, inverting the flask so the solvent flows to a second bulbous portion of the flask, returning the flask to an upright position, opening the flask mouth, and adding a pre-measured sample through the open flask mouth;
   (c) Closing and shaking the flask to substantially dissolve or solubilize the sample; and
   (d) Shaking the resulting solution down through a neck channel of the flask into the first bulbous portion, and taking a reading using graduated markings on the neck.

14. The process according to claim 13, wherein the solvent is a 7:3 mixture of nitric acid and hydrochloric acid.

15. The process according to claim 13, wherein the first bulbous portion is at least twice as large as the second bulbous portion.

16. The process according to claim 15, further comprising the step of:

(e) Repeat the procedure three times, and perform a statistical analysis on the results.

17. The process according to claim 16, wherein the solvent is deionized water.

18. The volumetric densiometer flask according to claim 2, wherein the markings, which are on the outside of the neck, comprise: a zero mark; a plurality of first volume marks on the neck exceeding the zero mark; and a plurality of second volume marks less than the zero mark in the same increments as the first volume marks.

19. The volumetric densiometer flask according to claim 1, wherein a diameter of the flask neck is determined by the following:

$$\Pi r^2 h = v$$

where: r=radius of the central channel; h=height of the neck; v=volume of the neck.

* * * * *